United States Patent [19]

Endo et al.

[11] Patent Number: 5,569,464
[45] Date of Patent: Oct. 29, 1996

[54] STABLE AQUEOUS DISPERSIONS CONTAINING LIPOSOMES

[75] Inventors: Kenji Endo, Fujisawa; Hidekazu Suzuki, Kanagawa-ken; Touru Oguma, Hadano; Masayoshi Goto, Tokyo, all of Japan

[73] Assignee: Wakamoto Pharmaceutical Co., Ltd., Tokyo, Japan

[21] Appl. No.: 448,972

[22] Filed: May 24, 1995

Related U.S. Application Data

[63] Continuation of Ser. No. 216,854, Mar. 24, 1994, abandoned.

[30] Foreign Application Priority Data

Apr. 2, 1993 [JP] Japan ..................... 5-098367

[51] Int. Cl.⁶ ................................ A61K 9/127
[52] U.S. Cl. ...................... 424/450; 428/402.2
[58] Field of Search ................ 424/450; 428/402.2

[56] References Cited

U.S. PATENT DOCUMENTS 4,946,683  8/1990  Forssen .......................... 424/422

FOREIGN PATENT DOCUMENTS

| | | |
|---|---|---|
| 1280975 | 3/1991 | Canada. |
| 0211647 | 2/1987 | European Pat. Off.. |
| 0467275 | 1/1992 | European Pat. Off.. |
| 0472225 | 2/1992 | European Pat. Off.. |
| 2660192 | 10/1991 | France. |
| 0046921 | 3/1982 | Japan. |
| 2-273539 | 11/1990 | Japan. |
| 2-295917 | 12/1990 | Japan. |
| 2103485 | 2/1983 | United Kingdom. |

OTHER PUBLICATIONS

Abstract of Japanese patent application JP2273539, Nov. 1990, Derwent Publications Ltd.

*Primary Examiner*—Gollamudi S. Kishore
*Attorney, Agent, or Firm*—Burns, Doane, Swecker & Mathis, LLP

[57] ABSTRACT

An aqueous dispersion containing liposomes comprising yolk lecithin and/or soybean lecithin as lipids for forming liposomes wherein the dispersion contains a hydroxy acid and an amino acid, which hardly shows coloration, shows little leak of drugs encapsulated in the liposomes and is stable in a broad pH range.

7 Claims, No Drawings

STABLE AQUEOUS DISPERSIONS CONTAINING LIPOSOMES

This application is a continuation, of application Ser. No. 08/216,854, filed Mar. 24, 1994 abandoned.

BACKGROUND OF THE INVENTION

1. Field of the Invention

The present invention relates to an aqueous dispersion containing liposomes. More specifically, the present invention relates to an aqueous dispersion containing liposomes containing a hydroxy acid and an amino acid as stabilizing agents.

2. Prior Art

Liposomes are vesicles composed of lipid bilayer membranes and their applications have recently been developed in various fields such as drug delivery systems, diagnostic drugs, artificial enzyme carriers, sensors and cosmetics. In particular, liposomes encapsulating drugs have been actively developed for the purposes of stabilization of unstable drugs, slow release of drugs in living bodies and targeting of drugs to lesion sites. However, liposomes themselves are often unstable to heat and it has been known that, even though they are prepared as a suspension, they relatively rapidly exhibit aggregation or fusion with one another as well as precipitation and coloration. Thus, these problems have been great problems of the commercialization of liposome formulations.

Hitherto, some studies have been conducted to improve the storage stability of liposomes. However, many of them mainly aimed at repressing the aggregation of liposomes, preventing the precipitation of liposomes and preventing the leak of encapsulated materials, and much attention has not been paid to the change of apparent color, i.e., the coloration, which can be very easily recognized upon their practical use. This coloring phenomenon has been known to be caused by the degradation products which are given by the peroxidation degradation of phospholipids generally used as lipids for forming liposomes. As a solution of this problem, there have been proposed liposome formulations where vitamin E is added to the lipids for forming liposomes (Japanese Patent Application Laid-Open (KOKAI) No. 2-295917). However, vitamin E itself is very unstable to heat, light and oxygen and has a problem of giving change of color upon its degradation.

On the other hand, Japanese Patent Application Laid-Open (KOKAI) No. 62-42733 discloses that liposomes were prepared by using dipalmitoylphosphatidylcholine, a synthetic phospholipid, as a lipid for forming liposomes and specific hydrating agents and sterilized by heat and these liposomes were stable without change of color after one year storage at room temperature. However, the stabilizing effect of the hydrating agents on liposomes prepared by using yolk lecithin or soybean lecithin was not described or suggested at all. Moreover, the liposomes composed of synthetic phospholipids have a problem from an economical point of view since they are very expensive even though they are more stable than those composed of natural phospholipids.

SUMMARY OF THE INVENTION

The present inventors have diligently studied to obtain an aqueous dispersion containing liposomes which shows good storage stability by using natural phospholipids which are inexpensive and have high safety as lipids for forming liposomes. As a result, it has been found that the change of color of liposomes, when they are stored in the form of an aqueous dispersion, can be prevented by adding a hydroxy acid and an amino acid to the aqueous dispersions containing liposomes composed of natural phospholipids and containing no drugs. Moreover, it has been also found that the same effect can be attained as to the aqueous dispersions containing liposomes containing drugs and completed the present invention.

Therefore, according to the present invention, there is provided an aqueous dispersion containing liposomes comprising yolk lecithin and/or soybean lecithin as lipids for forming liposomes, which dispersion contains one or more hydroxy acids and one or more amino acids.

It has been also found that the leak of drugs encapsulated in the liposomes can be prevented in the liposomes according to the present invention. Moreover, while conventional aqueous dispersions containing liposomes have been known to be preferentially stable at a neutral pH of 6 to 7 and such stability is not yet considered sufficient for practical use, an aqueous dispersion containing liposomes which has a practical stability not only at a neutral pH but also in a broad pH range of 4 to 12 can be provided by the present invention.

DESCRIPTIONS OF THE PREFERRED EMBODIMENTS

The present invention will be described in detail hereinafter.

As the "lipid for forming liposomes" of the present invention, there can be mentioned those comprising yolk lecithin and/or soybean lecithin. So long as the lipids have a composition comprising the above lecithins, any lipids can be used for the present invention. That is, the advantages of the present invention can also be obtained by using the above lecithins mixed with the above lecithins in a hydrogenated form, synthetic phospholipids such as dimyristoylphosphatidylcholine, dipalmitoylphosphatidylcholine, distearoylphosphatidylcholine, dicetylphosphate and phosphatidylglycerol.

For preparing an aqueous dispersion containing liposomes of the present invention, these lipids for forming liposomes are normally used in an amount of from 0.0001 to 0.1 parts by weight, preferably from 0.001 to 0.05 parts by weight based on a part by weight of water.

A membrane-forming adjuvant may be added to these lipids for forming liposomes, if desired. As the membrane-forming adjuvant, sterols such as cholesterol, aliphatic amines and fatty acids such as stearylamine and oleic acid can be exemplified. The amount of these membrane-forming adjuvants is not particularly limited and is normally from 0.05 to 0.5 parts by weight for the sterols and from 0.05 to 0.2 parts by weight for the aliphatic amines and fatty acids based on a part by weight of the lipids for forming liposomes.

The hydroxy acid used for the present invention is not particularly limited, but one or more of members selected from lactic acid, tartaric acid, malic acid, citric acid and pharmaceutically acceptable salts thereof are preferably used. Among these hydroxy acids, citric acid and its pharmaceutically acceptable salts are particularly preferred.

The amino acid is not also particularly limited, but one or more of members selected from glycine, alanine, leucine, serine, histidine, proline, hydroxyproline, cysteine, methionine, lysine, arginine, glutamic acid, aspartic acid and pharmaceutically acceptable salts thereof are preferably used.

Among these amino acids, methionine, histidine, arginine, glutamic acid, aspartic acid and their pharmaceutically acceptable salts are particularly preferred.

The essential characteristics of the present invention reside in the use of at least one of the above hydroxy acids and at least one of the above amino acids in combination. Therefore, several kinds of the above hydroxy acids and several kinds of the above amino acids may be used in combination, and it is not intended to exclude using mixtures of more than two kinds of the compounds.

Furthermore, the concentration ranges of the hydroxy acids and the amino acids where the advantages can be obtained may be somewhat varied depending on the kinds of the hydroxy acid and the amino acid used in combination.

For example, when sodium citrate and methionine are used, from 0.05 to 5 parts by weight of sodium citrate (in terms of citric acid) and from 0.008 to 0.8 parts by weight of methionine can be suitably used with a part by weight of lipids for forming liposomes.

When sodium citrate and histidine hydrochloride are used, from 0.05 to 5 parts by weight of sodium citrate (in terms of citric acid) and from 0.0006 to 0.3 parts by Weight of histidine hydrochloride (in terms of histidine) can be suitably used with a part by weight of lipids for forming liposomes.

When sodium citrate and arginine are used, from 0.05 to 5 parts by weight of sodium citrate (in terms of citric acid) and from 0.02 to 4 parts by weight of arginine can be suitably used with a part by weight of lipids for forming liposomes.

When sodium citrate and sodium glutamate or sodium aspartate are used, from 0.05 to 5 parts by weight of sodium citrate (in terms of citric acid) and from 0.015 to 3 parts by weight of sodium glutamate or sodium aspartate (in terms of glutamic acid or aspartic acid) can be suitably used with a part by weight of lipids for forming liposomes.

The advantages of the present invention can be attained by using a hydroxy acid and an amino acid in combination in amounts within the above proportion with respect to lipids for forming liposomes. On the other hand, when the amount of the these stabilizing agents in an aqueous dispersion containing liposomes is greater than a certain amount, the operability of the dispersion will be declined because of the increase of viscosity of the dispersion and phase separation will be occurred because of floating of liposomes and they are not preferred. Moreover, when the amount of the amino acid exceeds a certain amount, decrease of the stabilizing effect is observed. Therefore, for a part by weight of an aqueous dispersion containing liposomes, it is normally preferred that not more than 0.13 parts by weight of the hydroxy acid and, while the upper limit of the amount of the amino acid is varied depending on its kind, not more than 0.02 parts by weight of methionine, 0.015 parts by weight of histidine, 0.05 parts by weight of arginine or 0.08 parts by weight of glutamic acid or aspartic acid are used.

The drugs to be contained in the liposomes of the present invention are not particularly limited and may be either hydrophilic or lipophilic. For example, they may be agents affecting central nervous system, agents affecting peripheral nervous system, cardiovascular agents, agents affecting respiratory organs, agents affecting digestive organs, hormone preparations, vitamin preparations, agents related to blood and body fluids, agents affecting metabolism, carcinostatic agents, antiallergic agents, antibiotics preparations, chemotherapeutics, agents for ophthalmic use, diagnostic agents, analgesics and sedatives agents, physiologically active substances, prostaglandin agents, immunoregulatory drugs, anti-inflammatory agents and the like. Examples of these agents are set forth below, but the present invention is not limited to them:

(1) agents affecting central nervous system such as:
  a) hypnotics and sedatives and antianxiety agents such as alprazolam and diazepam;
  b) antiepileptics such as phenobarbital;
  c) antipyretics, analgesics and antiinflammatory agent such as pranoprofen and ketoprofen;
  d) psychotropic agents such as amitriptyline and chlorpromazine;

(2) agents affecting peripheral nervous system such as;
  a) local anesthetics such as lidocaine, benzocaine, tetracaine and dibucaine;
  b) antispasmodics such as atropine and afloqualone;

(3) cardinovascular agents such as;
  a) antihypertensives such as reserpine and hydralazine;
  b) vasoconstrictors such as phenylephrine, naphazoline and methoxamine;
  c) vasodilators such as diltiazem and nifedipine; d) antihyperlipemnia agents such as clofibrate and pravastatin;

(4) agents affecting respiratory organs such as:
  a) antitussives such as methylephedrine and ephedrine;
  b) bronchodilators such as theophylline; and pharmaceutically acceptable salts thereof.

(5) agents affecting digestive organs such as:
  a) antiulcer agents such as farnesol, geraniol and 2-N-{3-[3-(1-piperidinomethyl)phenoxy] propyl}amino-5-amino-1,3,4-thiadiazole (hereinafter abbreviated as "TAS");

(6) hormone preparations such as;
  a) adrenal hormone preparations such as betamethasone phosphate, dexamethasone phosphate, hydrocortisone, triamcinolone and prednisolone;
  b) hormone preparations such as insulin;

(7) vitamin preparations such as vitamin A and preparations and vitamin C and preparations;

(8) agents related to blood and body fluids such as:
  a) hemostatics such as carbazochrome, tranexamic acid;

(9) agents affecting metabolism such as;
  a) agents for liver disease such as glycyrrhizic acid•DL-methionine;
  b) enzyme preparations such as superoxide dismutase, urokinase and t-PA
  c) agents for diabetic complications such as epalrestat;

(10) carcinostatic agents such as mitomycin, adriamycin, methotrexate, cisplatin, tegafur, vincristine and doxorubicin;

(11) antiallergic agents such as;
  a) antihistamines such as chlorpheniramine and diphenhydramine;
  b) antiallergic agents such as cromoglicic acid, tranilast and ketotifen;

(12) antibiotics preparations such as amphotericin B, gentamicin, erythromycin, tetracycline, chloramphenicol and colistin methanesulfonic acid;

(13) chemotherapeutics such as ofloxacin, norfloxacin and miconazole;

(14) agents for ophthalmic use such as;
  a) antiglaucoma drugs such as epinephrine, timolol and carteolol;
  b) anticataract drugs such as glutathione and pirenoxine;

c) mydriatics and preparations such as tropicamide;

d) miotics and preparations such as pilocarpine and carbachol;

(15) diagnostic agents such as fluorescein;

(16) analgesics and sedatives agents such as morphine and codeine;

(17) physiologically active substances such as erythropoietin;

(18) prostaglandin agents such as prostaglandin $E_1$ and prostaglandin $A_1$;

(19) immunoregulatory drug such as interferon, interleukin, muramyl dipeptide, muramyl tripeptide, penicillamine and ciclosporin;

(20) anti-inflammatory agents such as fluorometholone, glycyrrhizic acid and dicrofenac;

As examples of the "pharmaceutically acceptable salts" of the hydroxy acids, the amino acids and the drugs used for the present invention, sodium salts, potassium salts and the like can be mentioned for the hydroxy acids, glutamic acid, dicrofenac, betamethasone phosphate and the like, hydrochloride salts, sulfate salts and the like can be mentioned for arginine, histidine, gentamicin, morphine, lidocaine, pilocarpine and the like, and maleate salts and the like can be mentioned for chlorpheniramine and timolol.

The process for preparing the aqueous dispersion containing liposomes of the present invention will be explained. Though various known methods are applicable, it can be prepared, for example, as follows. The lipids for forming liposomes comprising yolk lecitin and, if desired, cholesterol and the like as membrane-forming adjuvants are dissolved in a suitable solvent such as chloroform and the solvent is evaporated in vacuo to prepare a lipid film. This film is suspended in water, and a hydroxy acid and an amino acid are added to give an aqueous dispersion containing liposomes of the present invention. Alternatively, the lipid film prepared as above can be suspended in a solution containing a hydroxy acid and an amino acid to give an aqueous dispersion containing liposomes of the present invention. Moreover, an aqueous dispersion containing liposomes encapsulating drugs according to the present invention can be prepared as follows. When the drug is a hydrophilic drug, the drug may be dissolved in water or a solution containing a hydroxy acid and an amino acid for supending the lipid film, and the liposomes may be prepared as the same manner as above. When the drug is a lipophilic drug, the drug may be mixed in the organic solvent with lipids for forming liposomes and, if desired, membrane-forming adjuvants and the liposomes can be prepared as the same manner as above. With respect to the aqueous dispersion containing liposomes obtained as above, if necessary, encapsulation efficiency of drugs can be increased by repeating freeze-thawing process, or the size distribution of the liposomes can be controlled by the extrusion method (M. J. Hope, M. B. Bally, G. Webb and P. R. Cullis,: Biochim. Biophys. Acta 812, 55 (1985)) or the like. The drugs which are not encapsulated in the liposomes can be removed by gel filteration, centrifugal separation, affinity chromatography or the like.

The uses of the aqueous dispersion containing liposomes obtained as described above are expected in various applications and it may be used, for example, as cosmetics such as moisture-holding agents for skin care and as pharmaceutical preparations such as parenteral injections, eye drops, nasal drops, endermic agents, inhalation agents and oral agents In preparing the aqueous dispersion containing liposomes of the present invention as formulations such as those described above, conventional additives such as isotonic agents, pH adjusting agents, antiseptic agents and stabilizing agents may be added so long as the advantages of the dispersion according to the present invention are not deteriorated. Moreover, the aqueous dispersion containing liposomes of the present invention may be subjected to a sterilizing treatment by a fractional sterilization method. The stability of the dispersion is not decreased by this treatment. Furthermore, as a method for preventing oxidation of parenteral injection and the like, nitrogen gas substitution is generally employed when a liquid preparation is filled in ampouls and the like. Though the aqueous dispersion containing liposomes of the present invention is stable without the nitrogen gas substitution, a greater stability can be expected by employing such nitrogen gas substitution.

EXAMPLES

The present invention will be further illustrated by referring to the following examples, but it is not intended to restrict the present invention to the examples. The term "percent (%)" used in the following examples means "percent by weight" excepting those used for encapsulation efficiency and drug-remaining ratio.

Stability of dispersion was evaluated by determining degree of coloration, relative encapsulation efficiency and drug-remaining ratio. The degree of apparent coloration was evaluated by determining color difference ($\Delta E$) between samples before and after storage by means of a color difference meter (Model ND-504 DE: Nihon Densyoku Industry Co.,Ltd.). Coordinate values based on the UCS system of color representation, L, a and b, were measured by the color difference meter with respect to the same samples before and after the storage, and the values of $\Delta E$ were calculated in accordance with the following equation:

$$\Delta E = \{(L_1-L_2)^2 + (a_1-a_2)^2 + (b_1-b_2)^2\}^{1/2}$$

In the above equation, $L_1$, $a_1$ and $b_1$ are the measured values obtained for a sample before storage and $L_2$, $a_2$ and $b_2$ are for a sample after storage.

The $\Delta E$ values obtained in the following examples were classified into the 5 ranges shown below and represented by the appended term or symbols as the evaluation of appearance.

No change: $\Delta E < 2.5$

\* (Faint yellow): $2.5 \leq \Delta E < 3.5$

\*\* (Light yellow): $3.5 \leq \Delta E < 5.0$

\*\*\* (Yellow): $5.0 \geq \Delta E < 8.0$

\*\*\*\* (Yellowish brown): $\Delta E \geq 8.0$

The relative encapsulation efficiency (%) and the drug-remaining ratio (%) were calculated in accordance with the following equations, respectively:

Relative encapsulation efficiency (%) =

$$\frac{\text{Encapsulation efficiency after storage (\%)}}{\text{Encapsulation efficiency before storage (\%)}} \times 100$$

Drug-remaining ratio (%) =

$$\frac{\text{Total drug concentration after storage}}{\text{Total drug concentration before storage}} \times 100$$

In the above equations, the "total drug concentration" is obtained as follows. First, a drug concentration of liquid obtained by treating an aqueous dispersion containing liposomes with Triton X-100 to destroy liposomes contained in the dispersion is determined. Then, the total drug concentration is calculated from the above-obtained drug concentration of the liquid so that the total drug concentration expresses the drug concentration in the original dispersion. Further, the "encapsulation efficiency" was obtained in accordance with the following equation:

Encapsulation efficiency (%) =

$$\frac{\text{Total drug concentration} - \text{Unencapsulated drug concentration}}{\text{Total drug concentration}} \times 100$$

In the above equation, the term "total drug concentration" has the same meaning as above and the term "unencapsulated drug concentration" is determined as a drug concentration in a filtrate obtained from ultrafiltration of an aqueous dispersion for removing the liposomes.

Example 1

0.25 g of egg phosphatidylcholine (PC purity: more than 95%, Nihon Yushi Co.,Ltd.) and 0.125 g of cholesterol were dissolved in 20 ml of a chloroform/methanol mixture (10:1) and the solvent was removed by an evaporator to form a lipid film.

5 ml of phosphate buffer of pH 7.4 (made isotonic with sodium chloride) was added to this lipid film and strongly vortexed, and the obtained liquid was extruded under pressure through a polycarbonate membrane filter having a pore size of 0.2 μm (NUCLEPORE®: available from Nomura Microscience Co.,Ltd.) to obtain a milk white liposome stock dispersion of which liposomes contained egg phosphatidylcholine. Moreover, a milk white liposome stock dispersion of which liposomes contained soybean lecithin (phosphatidylcholine) was obtained in a manner similar to the above by using soybean lecithin (PC purity: 97.3%, Nihon Seika Col,Ltd.) instead of the egg phosphatidylcholine.

To one part by volume of the obtained liposome stock dispersions, one part by volume of a solution containing a hydroxy acid and one or more amino acids selected from various hydroxy acids and amino acids was added to obtain aqueous dispersions containing liposomes of the present invention. For comparison, to one part by volume of the above liposome stock dispersions, one part by volume of phosphate buffer containing a hydroxy acid or an amino acid alone, or one part by volume of phosphate buffer containing no stabilizing agents was added to give comparative aqueous dispersions containing liposomes.

These dispersions were filled into 1 ml glass ampoules and stored at 60° C. to be examined the change of their appearance. The changes of appearance after one-week storage are shown in Table 1. When any stabilizing agents (hydroxy acids and amino acids) are not used, or when a hydroxy acid or an amino acid is used alone, coloration was observed. On the other hand, the aqueous dispersions containing liposomes according to the present invention hardly exhibited change of appearance as compared with the dispersions before storage and therefore it was found that the aqueous dispersions containing liposomes according to the present invention were stable.

TABLE 1

| Lipid for forming liposomes[1] | Stabilizing agents[2] (part by weight) | | Appearance[3] |
|---|---|---|---|
| | Hydroxy acid | Amino acid | |
| | Present invention | | |
| York lecithin | Lactic acid (0.08) | Sodium glutamate (0.06) | No change |
| York lecithin | Malic acid (0.08) | Sodium glutamate (0.06) | No change |
| York lecithin | Tartaric acid (0.08) | Sodium glutamate (0.06) | No change |
| York lecithin | Sodium citrate (0.05) | Sodium glutamate (0.06) | No change |
| York lecithin | Malic acid (0.08) | Methionine (0.08) | No change |
| York lecithin | Malic acid (0.08) | Histidine hydrochloride (0.06) | * |
| York lecithin | Malic acid (0.08) | Serine (0.08) | * |
| York lecithin | Malic acid (0.08) | Arginine (0.08) | No change |
| York lecithin | Malic acid (0.08) | Sodium aspartate (0.06) | No change |
| York lecithin | Sodium citrate (0.05) | Methionine (0.08) | No change |
| York lecithin | Sodium citrate (0.05) | Histidine hydrochloride (0.06) | No change |
| York lecithin | Sodium citrate (0.05) | Serine (0.08) | No change |
| York lecithin | Sodium citrate (0.05) | Arginine (0.08) | No change |
| York lecithin | Sodium citrate (0.05) | Sodium aspartate (0.06) | No change |
| York lecithin | Sodium citrate (0.05) | Methionine + Sodium aspartate (0.04 + 0.03) | No change |
| York lecithin | Sodium citrate (0.05) | Methionine + Arginine (0.04 + 0.04) | No change |
| York lecithin | Sodium citrate (0.05) | Methionine + Histidine hydrochloride (0.04 + 0.03) | No change |

TABLE 1-continued

| Lipid for forming liposomes[1] | Stabilizing agents[2] (part by weight) | | Appearance[3] |
|---|---|---|---|
| | Hydroxy acid | Amino acid | |
| York lecithin | Sodium citrate (0.05) | Sodium aspartate + Arginine (0.03 + 0.04) | No change |
| York lecithin | Sodium citrate (0.05) | Sodium aspartate + Histidine hydrochloride (0.03 + 0.03) | No change |
| York lecithin | Sodium citrate (0.05) | Arginine + Histidine hydrochloride (0.04 + 0.03) | No change |
| Soybean lecithin | Sodium citrate (0.05) | Sodium aspartate (0.06) | No change |
| Comparative examples | | | |
| York lecithin | — | — | **** |
| York lecithin | Lactic acid (0.16) | — | **** |
| York lecithin | Malic acid (0.16) | — | **** |
| York lecithin | Tartaric acid (0.16) | — | **** |
| York lecithin | Sodium citrate (0.1) | — | * |
| York lecithin | — | Methionine (0.16) | ** |
| York lecithin | — | Histidine hydrochloride (0.12) | *** |
| York lecithin | — | Serine (0.16) | *** |
| York lecithin | — | Arginine (0.12) | ** |
| York lecithin | — | Sodium aspartate (0.12) | ** |
| York lecithin | — | Sodium glutamate (0.12) | * |
| Soybean lecithin | — | — | **** |
| Soybean lecithin | Sodium citrate (0.1) | — | * |
| Soybean lecithin | — | Sodium aspartate (0.12) | ** |

[1] The concentration of the lipids for forming liposomes was 25 mg/ml.
[2] The amounts of the added stabilizing agents are shown in terms of parts by weight based on a part by weight of the lipids for forming liposomes. The amounts of the salts are represented by the amounts calculated as their free forms.
[3] Appearance was examined after one-week storage at 60° C.
*: Faint yellow, : Light yellow, *: Yellow, ****: Yellowish brown Example 2

To one part by volume of the liposome stock dispersion containing egg phosphatidylcholine obtained in Example 1, one part by volume of a solution containing sodium citrate and methionine, histidine hydrochloride, arginine or sodium glutamate at various concentrations was added to give aqueous dispersions containing liposomes, of which concentrations of the stabilizing agents are shown in Table 2.

These dispersions were stored at 60° C. and their changes of appearance were examined in a manner similar to Example 1. The changes of appearance after two-week storage were shown in Table 2. It was found that the advantage of the present invention is effectively obtained by using, with one part by weight of the lipids for forming liposomes, 0.05 to 5 parts by weight of citric acid together with one of the amino acids of the following amounts; 0.008 to 0.8 parts by weight for methionine, 0.0006 to 0.3 parts by weight for histidine, 0.02 to 2 parts by weight for arginine and 0.015 to 3 parts by weight for glutamic acid.

TABLE 2

| Stabilizing Agent[1] (part by weight) | | Appearance[2] |
|---|---|---|
| Sodium citrate | Amino acid | |
| | Methionine | |
| 0.05 | 0.8 | * |
| 0.05 | 0.08 | No change |
| 0.05 | 0.008 | * |
| 0.05 | 0.004 | ** |
| 0.05 | 0 | **** |
| | Histidine hydrochloride | |
| 0.05 | 0.6 | ** |
| 0.05 | 0.3 | * |
| 0.05 | 0.0006 | * |
| 0.05 | 0.0003 | ** |

TABLE 2-continued

| Stabilizing Agent[1] (part by weight) | | Appearance[2] |
|---|---|---|
| Sodium citrate | Amino acid | |
| | Arginine | |
| 0.05 | 4 | ** |
| 0.05 | 2 | * |
| 0.05 | 0.02 | * |
| 0.05 | 0.008 | *** |
| | Sodium glutamate | |
| 0.05 | 6 | ** |
| 0.05 | 3 | * |
| 0.05 | 0.015 | * |
| 0.05 | 0.006 | *** |
| | Methionine | |
| 5 | 0.08 | No change |
| 0.05 | 0.08 | No change |
| 0.025 | 0.08 | ** |
| 0 | 0.08 | *** |
| 0 | 0 | **** |
| | Histidine hydrochloride | |
| 5 | 0.06 | No change |
| 0.05 | 0.06 | No change |
| 0.005 | 0.06 | ** |
| 0 | 0.06 | *** |
| | Arginine | |
| 5 | 0.08 | No change |
| 0.05 | 0.08 | * |
| 0.005 | 0.08 | ** |
| 0 | 0.08 | *** |
| | Sodium glutamate | |
| 5 | 0.06 | No change |
| 0.05 | 0.06 | No change |
| 0.005 | 0.06 | ** |
| 0 | 0.06 | *** |

[1] The amounts of the added stabilizing agents are shown in terms of parts by weight based on a part by weight of the lipids for forming liposomes. The amounts of the salts are represented by the amounts calculated as their free forms. (The concentration of the lipids for forming liposomes was 25 mg/ml.)
[2] Appearance was examined after two-week storage at 60° C.
*: Faint yellow, : Light yellow, *: Yellow, ****: Yellowish brown Example 3

Various lipids for forming liposomes shown in Table 3 were dissolved in a chloroform/methanol mixture (10:1) and the solvent was removed by an evaporator to form lipid films having various compositions.

5 ml of Britton-Robinson buffer of pH 7.0 was added to each film and strongly vortexed, and the obtained liquids were extruded under pressure through a polycarbonate membrane filter having a pore size of 0.2 μm (NUCLEPORE®: available from Nomura Microscience Co.,Ltd.) to give liposome stock dispersions having various lipid compositions.

One part by volume of a solution containing 4% of sodium citrate and 0.4% of sodium glutamate was added to one part by volume of the liposome stock dispersions obtained above to give aqueous dispersions containing liposomes according to the present invention. For comparison, one part by volume of the Britton-Robinson buffer was added to one part by volume of each of the above liposome stock dispersions to give comparative aqueous dispersions containing liposomes.

These dispersions were stored at 60° C. in a manner similar to Example 1. The changes of appearance after one-week storage were shown in Table 3. When the stabilizing agents were not used, coloration was observed. As opposed to that, the aqueous dispersions containing liposomes according to the present invention hardly exhibited change of appearance as compared with the dispersions before storage. Therefore, it was found that the advantage of the present invention, the stabilizing effect, can be obtained in the aqueous dispersions containing liposomes having various lipid composition containing yolk lecithin or soybean lecithin.

TABLE 3

| Lipid composition[1] (Molar ratio) | Stabilizing agent[2] (part by weight) | Appearance[3] |
|---|---|---|
| Present invention | | |
| EPC/DMPC (1:0.1) | Sodium citrate + Sodium glutamate (0.5 + 0.06) | No change |
| EPC/DMPC (1:0.5) | Sodium citrate + Sodium glutamate (0.4 + 0.04) | No change |
| EPC/HEPC (1:0.1) | Sodium citrate + Sodium glutamate (0.5 + 0.06) | No change |
| EPC/DPPG (1:0.1) | Sodium citrate + Sodium glutamate (0.5 + 0.06) | No change |
| EPC/DPPA (1:0.1) | Sodium citrate + Sodium glutamate (0.5 + 0.06) | No change |
| EPC/Cho/DMPC(1:1:0.1) | Sodium citrate + Sodium glutamate (0.5 + 0.06) | No change |
| SPC/Cho/DMPC(1:1:0.1) | Sodium citrate + Sodium glutamate (0.5 + 0.06) | No change |
| Comparative examples | | |
| EPC/DMPC (1:0.1) | — | **** |
| EPC/DMPC (1:0.5) | — | **** |
| EPC/HEPC (1:0.1) | — | **** |
| EPC/DPPG (1:0.1) | — | **** |
| EPC/DPPA (1:0.1) | — | **** |
| EPC/Cho/DMPC(1:1:0.1) | — | **** |
| SPC/Cho/DMPC(1:1:0.1) | — | **** |

[1] EPC: Egg phosphatidylcholine
SPC: Soybean phosphatidylcholine
DMPC: Dimyristoylphosphatidylcholine
HEPC: Hydrogenated egg phosphatidylcholine
DPPG: Dipalmitoylphosphatidylglycerol
DPPA: Dipalmitoylphosphatidic acid
Cho: Cholesterol
[2] The amounts of the added stabilizing agents are shown in terms of parts by weight based on a part by weight of the lipids for forming liposomes. The amounts of the salts are represented by the amounts calculated as their free forms. (The concentrations of the lipids for forming liposomes were 27 to 36 mg/ml.)
[3] Appearance was examined after one-week storage at 60° C.
****: Yellowish brown Example 4

5 ml of Britton-Robinson buffer having a pH of 3 to 12 was added to the lipid film containing egg phosphatidylcholine prepared in Example 1 and strongly vortexed, and the obtained liquids were extruded under pressure through a polycarbonate membrane filter having a pore size of 0.2 μm (NUCLEPORE®: available from Nomura Microscience Co.,Ltd.) to give liposome stock dispersions having various pH values of 3 to 12.

To one part by volume of the above-obtained liposome stock dispersions having the pH values of 3 to 12, one part by volume portions of a solution containing 0.4 or 4% of sodium citrate and 0.4% of methionine and having the pH values of 3 to 12 were added to give aqueous dispersions containing liposomes having the pH value of 3 to 12 according to the present invention. For comparison, to one part by volume of the above liposome stock dispersions having the pH values of 3 to 12, one part by volume portions of the Britton-Robinson buffer of the same pH as the stock dispersions were added to give comparative aqueous dispersions containing liposomes having the pH values of 3 to 12.

These dispersions were stored at 60° C. and their changes of appearance were examined in a manner similar to Example 1. The changes of appearance after one-week storage were shown in Table 4. While remarkable coloration was observed in the comparative examples, the aqueous dispersions containing liposomes according to the present invention, which were added with sodium citrate and methionine, exhibited no change in a pH range of 4 to 12 as compared with the dispersions before storage and hence they were stable. Therefore, it was found that the advantage of the present invention, the stabilizing effect, can be obtained in the pH range of 4 to 12.

TABLE 4

| pH | Stabilizing agent[1] (part by weight) | Appearance[2] |
|---|---|---|
| 3 | Present invention | |
| | Sodium citrate + Methionine (0.05 + 0.08) | **** |
| | Sodium citrate + Methionine (0.5 + 0.08) | *** |
| | Comparative example | |
| | — | **** |
| 4 | Present invention | |
| | Sodium citrate + Methionine (0.05 + 0.08) | No change |
| | Sodium citrate + Methionine (0.5 + 0.08) | No change |
| | Comparative example | |
| | — | **** |
| 5 | Present invention | |
| | Sodium citrate + Methionine (0.05 + 0.08) | No change |
| | Sodium citrate + Methionine (0.5 + 0.08) | No change |
| | Comparative example | |
| | — | **** |
| 6 | Present invention | |
| | Sodium citrate + Methionine (0.05 + 0.08) | No change |
| | Comparative Example | |
| | — | **** |
| 7 | Present invention | |
| | Sodium citrate + Methionine (0.05 + 0.08) | No change |
| | Sodium citrate + Methionine (0.5 + 0.08) | No change |
| | Comparative Example | |
| | — | **** |
| 8 | Present invention | |
| | Sodium citrate + Methionine (0.05 + 0.08) | No change |
| | Comparative Example | |
| | — | **** |
| 9 | Present invention | |
| | Sodium citrate + Methionine (0.05 + 0.08) | No change |
| | Sodium citrate + Methionine (0.5 + 0.08) | No change |
| | Comparative Example | |
| | — | **** |
| 10 | Present invention | |
| | Sodium citrate + Methionine (0.5 + 0.08) | No change |
| | Comparative Example | |
| | — | **** |
| 11 | Present invention | |
| | Sodium citrate + Methionine (0.5 + 0.08) | No change |
| | Comparative Example | |
| | — | **** |
| 12 | Present invention | |
| | Sodium citrate + Methionine (0.5 + 0.08) | No change |
| | Comparative Example | |
| | — | **** |

[1] The amounts of the added stabilizing agents are shown in terms of parts by weight based on a part by weight of the lipid for forming liposomes. The amounts of the salts are represented by the amounts calculated as their free forms. (The concentration of the lipid for forming liposomes was 25 mg/ml.)
[2] Appearance was examined after one week storage at 60° C.
*: Yellow, **: Yellowish brown Example 5

5 ml of phosphate buffer (made isotonic with sodium chloride) of pH 8.3 was added to the lipid film prepared in Example 1 containing egg phosphatidylcholine and strongly vortexed, and the obtained liquid was extruded under pressure through a polycarbonate membrane filter having a pore size of 0.2 μm (NUCLEPORE®: available from Nomura Microscience Co.,Ltd.) to give a milk white liposome stock dispersion.

One part by volume of a solution containing 0.4% of sodium citrate and 0.4% of methionine was added to one part by volume of the liposome stock dispersion obtained above to give an aqueous dispersion containing liposomes according to the present invention where the outside aqueous phase of the liposomes contained the stabilizing agents.

Moreover, 10 ml of phosphate buffer (made isotonic with sodium chloride) of pH 8.3 containing 0.2% of sodium citrate and 0.2% of methionine was added to the lipid film prepared in Example 1 containing egg phosphatidylcholine and strongly vortexed, and the obtained liquid was extruded under pressure through a polycarbonate membrane filter having a pore size of 0.2 μm (NUCLEPORE®: available from Nomura Microscience Co.,Ltd.) to give an aqueous dispersion containing liposomes of the present invention where the inside and outside aqueous phases of the liposomes contained the stabilizing agents.

For comparison, one part of phosphate buffer containing no stabilizing agents was added to one part of the above liposome stock dispersion to give a comparative aqueous dispersion containing liposomes. Moreover, the above-obtained aqueous dispersion containing liposomes according to the present invention where the inside and outside aqueous phases of the liposomes contained the stabilizing agents was centrifuged at 100,000×g and the precipitated liposomes were dispersed again in the phosphate buffer to give a comparative aqueous dispersion containing liposomes where only the inside aqueous phases of the liposomes contained the stabilizing agents.

These dispersions were stored at 60° C. and the change of appearance was examined in a manner similar to Example 1. The changes of appearance after 2-week storage were shown in Table 5. When the stabilizing agents were not used and when they were added only to the inside aqueous phases of the liposomes, coloration was observed. On the other hand, the stabilizing agents were added to the inside and outside aqueous phases of the liposomes or only to the outside aqueous phase of liposomes, change was not observed as compared with the dispersions before storage. Therefore, it was found that the effect of the present invention is obtained by adding the stabilizing agents to the inside and outside aqueous phases of liposomes or to the outside aqueous phase of the liposomes.

TABLE 5

| Stabilizing agent[1] (part by weight) | Appearance[2] |
|---|---|
| Present invention | |
| Sodium citrate + Methionine (0.05 + 0.08) (outside aqueous phase of liposomes) | No change |
| Sodium citrate + Methionine (0.05 + 0.08) (outside and inside aqueous phases of liposomes) | No change |
| Comparative examples | |
| Sodium citrate + Methionine (0.05 + 0.08) (inside aqueous phase of liposomes) | *** |
| — | **** |

[1]The amounts of the added stabilizing agents are shown in terms of parts by weight based on a part by weight of the lipid for forming liposomes. The amounts of the salts are represented by the amounts calculated as their free forms. (The concentration of the lipid for forming liposomes was 25 mg/ml.)
[2]Appearance was examined after 2-week storage at 60° C.
*: Yellow, **: Yellowish brown Example 6

5 ml of phosphate buffer (made isotonic with sodium chloride) of pH 8.3 containing 0.4% of sodium betamethasone phosphate was added to the lipid film prepared in Example 1 containing egg phosphatidylcholine and strongly vortexed. This aqueous dispersion containing liposomes was frozen with dry ice/acetone and thawed in a water bath at 20° C. After repeating this freeze-thawing process eight times, the dispersion was extruded under pressure through a polycarbonate membrane filter having a pore size of 0.2 μm (NUCLEPORE ®: available from Nomura Microscience Co.,Ltd.). Further, this aqueous dispersion containing liposomes was centrifuged at 100,000×g to remove unencapsulated drug and was dispersing again the precipitated liposomes in phosphate buffer to give a liposome stock dispersion containing sodium betamethasone phosphate.

0.25 parts by volume of phosphate buffer containing 1.6% of sodium citrate and 0.8% of sodium aspartate or one part by volume of phosphate buffer containing 0.4% sodium citrate and 0.2% of sodium aspartate was added to one part by volume of the liposome stock dispersion obtained above to give aqueous dispersions containing liposomes according to the present invention having concentrations of the lipid for forming liposomes of 0.04 and 0.025 parts by weight (based on a part by weight of the buffer where the lipid was dispersed). Moreover, the above liposome stock dispersion was diluted with phosphate buffer by five times or fifty times, and one part by volume of phosphate buffer containing 0.04% of sodium citrate and 0.02% of sodium aspartate or one part by volume of phosphate buffer containing 0.004% of sodium citrate and 0.002% of sodium aspartate was added to one part by volume of the diluted dispersions to give aqueous dispersions containing liposomes according to the present invention having a concentration of the lipid for forming liposomes of 0.0025 or 0.00025 parts by weight. For comparison, a dispersion was prepared in a manner similar to the above except that sodium citrate and sodium aspartate were not added.

These dispersions were stored at 60° C. in a manner similar to Example 1. Changes of appearance and relative encapsulation efficiencies after 2-week storage are shown in Table 6. When the stabilizing agents were not contained, change of appearance was observed and the relative encapsulation efficiency was remarkably decreased at a concentration of the lipid for forming liposomes of not less than 0.0025 parts by weight. When the concentration of the lipid for forming liposomes was 0.00025 parts by weight, though change of appearance was not observed at this concentration, the decrease of the relative encapsulation efficiency was remarkable. On the other hand, the aqueous dispersion containing liposomes of the present invention hardly exhibited change of appearance and the relative encapsulation efficiency was more than about 90% at all of the concentrations of the lipid for forming liposomes. Therefore, it was found that the aqueous dispersions containing liposomes of the present invention were stable regardless of the concentration of the lipid for forming liposomes.

TABLE 6

| Concentration of lipid for forming liposomes[1] | Stabilizing agent[2] | Appearance[3] | Relative encapsulation efficiency (%) |
|---|---|---|---|
| Present invention | | | |
| 0.04 | Sodium citrate + | * | 89.5 |
| 0.025 | Sodium aspartate | * | 90.9 |
| 0.0025 | (0.05 + 0.03) | No change | 100.0 |
| 0.00025 | | No change | 100.0 |
| Comparative examples | | | |
| 0.04 | | **** | 65.8 |
| 0.025 | Not present | **** | 49.0 |
| 0.0025 | | ** | 11.5 |
| 0.00025 | | No change | 2.8 |

[1]The concentrations of the lipid for forming liposomes are indicated in terms of parts by weight based on a part by weight of the buffer where the lipid was dispersed.
[2]The amounts of the added stabilizing agents are shown in terms of parts by weight based on a part by weight of the lipid for forming liposomes. The amounts of the salts are represented by the amounts calculated as their free forms.
[3]Appearance was examined after 2-week storage at 60° C.
*: Faint yellow, : Light yellow, **: Yellowish brown Example 7

To one part by volume of the liposome stock dispersion prepared in Example 6 containing sodium betamethasone phosphate, one part by volume of a solution containing sodium citrate and an amino acid selected from various amino acids was added to give aqueous dispersions containing liposomes of the present invention. For comparison, to one part by volume of the above liposome stock dispersion, one part by volume of phosphate buffer containing sodium citrate or an amino acid alone or phosphate buffer containing no stabilizing agents was added to give comparative aqueous dispersions containing liposomes.

These dispersions were stored at 60° C. in a manner similar to Example 1. Changes of appearance after one-week storage are shown in Table 7. When the stabilizing agents were not contained and when a hydroxy acid or an amino acid alone was added, coloration was observed. On the other hand, the aqueous dispersions containing liposomes of the present invention hardly exhibited change of appearance as compared with the dispersions before storage. Therefore, it was found that the aqueous dispersions containing liposomes of the present invention were stable even if they contained a drug.

TABLE 7

Liposomes encapsulating sodium betamethasone phosphate

Stabilizing agent[1] (part by weight)

| Hydroxy acid | Amino acid | Appearance[2] |
|---|---|---|
| *Present invention* | | |
| Sodium citrate (0.05) | Glycine (0.08) | No change |
| Sodium citrate (0.05) | Alanine (0.08) | No change |
| Sodium citrate (0.05) | Leucine (0.08) | No change |
| Sodium citrate (0.05) | Serine (0.08) | No change |
| Sodium citrate (0.05) | Proline (0.08) | No change |
| Sodium citrate (0.05) | Hydroxyproline (0.08) | No change |
| Sodium citrate (0.05) | Cysteine (0.08) | No change |
| Sodium citrate (0.05) | Lysine (0.08) | No change |
| Sodium citrate (0.05) | Sodium glutamate (0.06) | No change |
| Sodium citrate (0.05) | Sodium aspartate (0.06) | No change |
| *Comparative examples* | | |
| — | — | **** |
| Sodium citrate (0.05) | — | * |
| — | Glycine (0.08) | ** |
| — | Alanine (0.08) | ** |
| — | Leucine (0.08) | * |
| — | Serine (0.08) | ** |
| — | Proline (0.08) | * |
| — | Hydroxyproline (0.08) | ** |
| — | Cysteine (0.08) | ** |
| — | Lysine (0.08) | *** |
| — | Sodium glutamate (0.06) | * |
| — | Sodium aspartate (0.06) | * |

[1]The amounts of the added stabilizing agents are shown in terms of parts by weight based on a part by weight of the lipid for forming liposomes. The amounts of the salts are represented by the amounts calculated as their free forms. (The concentration of the lipid for forming liposomes was 25 mg/ml.)
[2]Appearance was examined after one-week storage at 60° C.
*: Faint yellow, : Light yellow, *: Yellow, ****: Yellowish brown

Example 8

(Liposomes encapsulating sodium betamethasone phosphate)

To one part by volume of the liposome stock dispersion prepared in Example 6 containing sodium betamethasone phosphate, one part by volume of a solution containing 4% of sodium citrate and 0.4 % of sodium glutamate was added to give an aqueous dispersion containing liposomes of the present invention. For comparison, a dispersion was prepared in a manner similar to the above except that sodium glutamate and sodium citrate were not added and nitrogen gas substitution was carried out when it was filled into ampoules.

These dispersions were stored at 60° C. to examine change of appearance in a manner similar to Example 1. Changes of appearance, relative encapsulation efficiencies and drug-remaining ratios after one or two-week storage are shown in Table 8. The comparative aqueous dispersion containing liposomes exhibited change of color with the lapse of time in spite of the nitrogen-substitution and, simultaneously, the encapsulation efficiency was decreased. On the other hand, the aqueous dispersion containing liposomes of the present invention exhibited no change of appearance even after two-week storage at 60° C. and maintained about 90% of the relative encapsulation efficiency and the drug-remaining ratio.

TABLE 8

Liposomes encapsulating sodium betamethasone phosphate

| | | Present invention Stabilizing agent Sodium citrate + Sodium glutamate (0.5 + 0.06) | Comparative example No stabilizing agent |
|---|---|---|---|
| After 1-week storage at 60° C. | Appearance[1] | No change | ** |
| | Relative encapsulation efficiency (%) | 94.9 | 82.4 |
| | Drug remaining ratio (%) | 93.5 | 91.5 |
| After 2-week storage at 60° C. | Appearance[1] | No change | *** |
| | Relative encapsulation efficiency (%) | 89.1 | 51.4 |
| | Drug-remaining ratio (%) | 92.2 | 87.4 |

[1]The amounts of the added stabilizing agents are shown in terms of parts by weight based on a part by weight of the lipid for forming liposomes. The amounts of the salts are represented by the amounts calculated as their free forms. (The concentration of the lipid for forming liposome was 25 mg/ml.)
[2]: Light yellow, *: Yellow,

Example 9

(Liposomes encapsulating morphine hydrochloride)

In a manner similar to Example 6 except that 5 ml of phosphate buffer of pH 6.0 (made isotonic with sodium chloride) containing 0.5% of morphine hydrochloride was used instead of 5 ml of phosphate buffer of pH 8.3 containing 0.4% of sodium betamethasone phosphate in Example 6, a liposome stock dispersion was obtained.

To one part by volume of the liposome stock dispersion obtained above, one part by volume of phosphate buffer containing 0.4% of sodium citrate and 0.4% of sodium glutamate was added to give an aqueous dispersion containing liposomes of the present invention. For comparison, to one part by volume of the above liposome stock dispersion of which liposomes encapsulated morphine, one part by volume of phosphate buffer containing 0.8% of sodium citrate or 0.8% of sodium glutamate alone or one part by volume of phosphate buffer containing no stabilizing agents was added to give comparative aqueous dispersions containing liposomes.

These dispersions were stored at 60° C. in a manner similar to Example 1. Changes of appearance, relative encapsulation efficiencies and drug-remaining ratios after 2-week storage are shown in Table 9. When the stabilizing agents were not used, change of appearance and remarkable decreases of the encapsulation efficiency and the drug-remaining ratio were observed. Moreover, when sodium citrate or sodium glutamate was added alone, though change of appearance and decrease of the drug-remaining ratio were slight, decrease of the relative encapsulation efficiency was remarkable. On the other hand, the aqueous dispersion containing liposomes of the present invention showed no change of appearance and no decrease of the drug-remaining ratio and maintained about 90% of the relative encapsulation efficiency.

From the results of Examples 8 and 9, it was found that the aqueous dispersion containing liposomes of the present invention can prevent change of appearance and, moreover, can prevent the leak of drugs.

TABLE 9

| | Liposomes encapsulating morphine hydrochloride | | |
|---|---|---|---|
| Stabilizing agent[1] (part by weight) | Appearance[2] | Relative encapsulation efficiency (%) | Drug-remaining ratio (%) |
| Present invention | | | |
| Sodium citrate + Sodium glutamate (0.05 + 0.06) | No change | 90.7 | 98.9 |
| Comparative examples | | | |
| Sodium citrate (0.1) | * | 80.5 | 95.7 |
| Sodium glutamate (0.12) | * | 79.3 | 97.5 |
| Not present | **** | 59.8 | 75.9 |

[1])The amounts of the added stabilizing agents are shown in terms of parts by weight based on a part by weight of lipid for forming liposomes. The amounts of the salts are represented by the amounts calculated as their free forms. (The concentration of the lipid for forming liposomes was 25 mg/ml.)
[2])Appearance was examined after 2-week storage at 60° C.
*: Faint yellow, ****: Yellowish brown Example 10

(Liposomes encapsulating sodium dexamethasone phosphate)

In a manner similar to Example 6 except that 5 ml of phosphate buffer of pH 8.3 containing 0.4% of sodium betamethasone phosphate in Example 6 was replaced with 5 ml of phosphate buffer of pH 8.3 containing 0.4% of sodium dexamethasone phosphate, a liposome stock dispersion containing sodium dexamethasone phosphate was obtained.

Example 11

(Liposomes encapsulating timolol maleate)

In a manner similar to Example 6 except that 5 ml of phosphate buffer of pH 8.3 containing 0.4% of sodium betamethasone phosphate in Example 6 was replaced with 5 ml of phosphate buffer of pH 8.0 containing 5% of timolol maleate, a liposome stock dispersion containing timolol maleate was obtained.

Example 12

(Liposomes encapsulating sodium dicrofenac)

5 ml of phosphate buffer (made isotonic with sodium chloride) of pH 8.0 containing 0.2% of sodium dicrofenac was added to the lipid film prepared in Example 1 containing egg phosphatidylcholine and strongly vortexed. The obtained aqueous dispersion containing liposomes was extruded under pressure through a polycarbonate membrane filter having a pore size of 0.2 μm (NUCLEPORE®: available from Nomura Microscience Co.,Ltd.) to give a liposome stock dispersion containing sodium dicrofenac.

Example 13

(Liposomes encapsulating fluorometholone)

0.25 g of egg phosphatidylcholine, 0.125 g of cholesterol and 1 mg of fluorometholone were dissolved in 40 ml of a hexane/methanol mixture (10:1), and the solvent was removed by an evaporator to form a lipid film containing fluorometholone. 5 ml of phosphate buffer (made isotonic with sodium chloride) of pH 8.0 was added to the lipid film and strongly vortexed, and the obtained aqueous dispersion containing liposomes was extruded under pressure through a polycarbonate membrane filter having a pore size of 0.2 μm (NUCLEPORE®: available from Nomura Microscience Co.,Ltd.) to give a liposome stock dispersion containing fluorometholone.

Example 14

(Liposomes encapsulating sodium pranoprofen)

In a manner similar to Example 12 except that 5 ml of phosphate buffer of pH 8.0 containing 0.2% of sodium dicrofenac in Example 12 was replaced with 5 ml of phosphate buffer of pH 7.0 containing 0.1% of sodium pranoprofen, a liposome stock dispersion containing sodium pranoprofen was obtained.

Example 15

(Liposomes encapsulating tegafur)

In a manner similar to Example 12 except that 5 ml of phosphate buffer of pH 8.0 containing 0.2% of sodium dicrofenac in Example 12 was replaced with 5 ml of Britton-Robinson buffer of pH 9.0 containing 4% of tegafur, a liposome stock dispersion containing tegafur was obtained.

Example 16

(Liposomes encapsulating gentamicin sulfate)

In a manner similar to Example 12 except that 5 ml of phosphate buffer of pH 8.0 containing 0.2% of sodium dicrofenac in Example 12 was replaced with 5 ml of Britton-Robinson buffer of pH 6.0 containing 0.3% of gentamicin sulfate, a liposome stock dispersion containing gentamicin sulfate was obtained.

Example 17

(Liposomes encapsulating chlorpheniramine maleate)

In a manner similar to Example 12 except that 5 ml of phosphate buffer of pH 8.0 containing 0.2% of sodium dicrofenac in Example 12 was replaced with 5 ml of Britton-Robinson buffer of pH 5.0 containing 0.5% of chlorpheniramine maleate, a liposome stock dispersion containing chlorpheniramine maleate was obtained.

Example 18

(Liposomes encapsulating sodium cromoglicate)

In a manner similar to Example 12 except that 5 ml of phosphate buffer of pH 8.0 containing 0.2% of sodium dicrofenac in Example 12 was replaced with 5 ml of Britton-Robinson buffer of pH 5.5 containing 2% of sodium cromoglicate, a liposome stock dispersion containing sodium cromoglicate was obtained.

Example 19

(Liposomes encapsulating urokinase)

In a manner similar to Example 12 except that 5 ml of phosphate buffer of pH 8.0 containing 0.2% of sodium dicrofenac in Example 12 was replaced with 5 ml of Britton-Robinson buffer of pH 7.0 containing 12,000 units/ml of urokinase, a liposome stock dispersion containing urokinase was obtained.

Example 20

(Liposomes encapsulating lidocaine hydrochloride)

In a manner similar to Example 12 except that 5 ml of phosphate buffer of pH 8.0 containing 0.2% of sodium dicrofenac in Example 12 was replaced with 5 ml of Britton-Robinson buffer of pH 6.0 containing 1% of lidocaine hydrochloride, a liposome stock dispersion containing lidocaine hydrochloride was obtained.

Example 21

(Liposomes encapsulating phenylephrine hydrochloride)

In a manner similar to Example 12 except that 5 ml of phosphate buffer of pH 8.0 containing 0.2% of sodium dicrofenac in Example 12 was replaced with 5 ml of Britton-Robinson buffer of pH 5.0 containing 0.5% of phenylephrine hydrochloride, a liposome stock dispersion containing phenylephrine hydrochloride was obtained.

Example 22

(Liposomes encapsulating pilocarpine hydrochloride)

In a manner similar to Example 12 except that 5 ml of phosphate buffer of pH 8.0 containing 0.2% of sodium dicrofenac in Example 12 was replaced with 5 ml of Britton-Robinson buffer of pH 5.0 containing 1% of pilocarpine hydrochloride, a liposome stock dispersion containing pilocarpine hydrochloride was obtained.

Example 23

(Liposomes encapsulating carbachol)

In a manner similar to Example 12 except that 5 ml of phosphate buffer of pH 8.0 containing 0.2% of sodium dicrofenac in Example 12 was replaced with 5 ml of Britton-Robinson buffer of pH 7.0 containing 0.75% of carbachol, a liposome stock dispersion containing carbachol was obtained.

Example 24

(Liposomes encapsulating TAS)

In a manner similar to Example 12 except that 5 ml of phosphate buffer of pH 8.0 containing 0.2% of sodium dicrofenac in Example 12 was replaced with 5 ml of Britton-Robinson buffer of pH 5.0 containing 0.2% of TAS, a liposome stock dispersion containing TAS was obtained.

Example 25

(Liposomes encapsulating prostaglandin $E_1$)

In a manner similar to Example 13 except that 1 mg of fluorometholon was replaced with 25 μg of prostaglandin $E_1$ and phosphate buffer of pH 8.0 was replaced with Britton-Robinson buffer of pH 5.0, a liposome stock dispersion containing prostaglandin $E_1$ was obtained.

Example 26

(Liposomes encapsulating tropicamide)

In a manner similar to Example 12 except that 5 ml of phosphate buffer of pH 8.0 containing 0.2% of sodium dicrofenac in Example 12 was replaced with 5 ml of Britton-Robinson buffer of pH 5.0 containing 0.5% of tropicamide, a liposome stock dispersion containing tropicamide was obtained.

Example 27

(Liposomes encapsulating glutathione)

In a manner similar to Example 12 except that 5 ml of phosphate buffer of pH 8.0 containing 0.2% of sodium dicrofenac in Example 12 was replaced with 5 ml of Britton-Robinson buffer of pH 6.0 containing 2% of glutathione, a liposome stock dispersion containing glutathione was obtained.

Example 28

(Liposomes encapsulating penicillamine)

To the lipid film prepared in Example 1 containing egg phosphatidylcholine, 5 ml of Britton-Robinson buffer of pH 5.0 containing 1% of penicllamine was added and strongly vortexed. The obtained aqueous dispersion containing liposomes was extruded under pressure through a polycarbonate membrane filter having a pore size of 0.2 μm (NUCLE-PORE®: available from Nomura Microscience Co.,Ltd.) and centrifuged at 100,000×g to remove unencapsulated drug and was dispersing again the precipitated liposomes in Brutton-Robinson buffer to give a liposome stock dispersion containing penicillamine.

To one part by volume of each of the liposome stock dispersions obtained in Examples 10 to 28 containing various drugs, one part by volume of Britton-Robinson buffer containing sodium citrate and sodium glutamate, sodium aspartate or histidine hydrochloride at a predetermined concentration was added to give aqueous dispersions containing liposomes of the present invention shown in Table 10. For comparison, to one part by volume of the above liposome stock dispersions, Britton-Robinson buffer containing sodium citrate or one of the aforementioned amino acids alone or Britton-Robinson buffer containing no stabilizing agents was added to give comparative aqueous dispersions containing liposomes.

These dispersions were stored at 60° C. in a manner similar to Example 1. Changes of appearance after one or two-week storage were shown in Table 10. Coloration was observed when the stabilizing agents were not used or when sodium citrate or an amino acid alone was added. As opposed to that, the aqueous dispersions containing liposomes of the present invention hardly exhibited change of appearance as compared with the dispersions before storage. From the above results, it was found that the aqueous dispersions containing liposomes of the present invention were stable whether the encapsulated drug was hydrophilic or lipophilic.

TABLE 10

| Example | Stabilizing agent[1] (part by weight) | Appearance[2] |
|---|---|---|
| 10 | Present invention | |
| | Sodium citrate + Sodium glutamate (0.5 + 0.06) | No change |
| | Comparative examples | |
| | Sodium citrate (1.0) | ** |

TABLE 10-continued

| Example | Stabilizing agent[1] (part by weight) | Appearance[2] |
|---|---|---|
| | Sodium glutamate (0.12) | *** |
| | Not present | **** |
| 11 | Present invention | |
| | Sodium citrate + Sodium glutamate (0.125 + 0.15) | No change |
| | Comparative examples | |
| | Sodium citrate (0.25) | ** |
| | Sodium glutamate (0.3) | * |
| | Not present | **** |
| 12 | Present invention | |
| | Sodium citrate + Sodium glutamate (0.125 + 0.06) | No change |
| | Comparative examples | |
| | Sodium citrate (0.25) | ** |
| | Sodium glutamate (0.12) | **** |
| | Not present | **** |
| 13 | Present invention | |
| | Sodium citrate + Sodium aspartate (0.05 + 0.06) | No change |
| | Comparative examples | |
| | Sodium citrate (0.1) | * |
| | Sodium aspartate (0.12) | *** |
| | Not present | **** |
| 14 | Present invention | |
| | Sodium citrate + Histidine hydrochloride (0.125 + 0.015) | No change |
| | Comparative examples | |
| | Sodium citrate (0.25) | * |
| | Histidine hydrochloride (0.03) | *** |
| | Not present | **** |
| 15 | Present invention | |
| | Sodium citrate + Histidine hydrochloride (0.25 + 0.006) | No change |
| | Comparative examples | |
| | Sodium citrate (0.5) | **** |
| | Histidine hydrochloride (0.012) | **** |
| | Not present | **** |
| 16 | Present invention | |
| | Sodium citrate + Histidine hydrochloride (0.25 + 0.006) | * |
| | Comparative examples | |
| | Sodium citrate (0.5) | ** |
| | Histidine hydrochloride (0.012) | **** |
| | Not present | **** |
| 17 | Present invention | |
| | Sodium citrate + Histidine hydrochloride (0.25 + 0.006) | No change |
| | Comparative examples | |
| | Sodium citrate (0.5) | * |
| | Histidine hydrochloride (0.012) | *** |
| | Not present | **** |
| 18 | Present invention | |
| | Sodium citrate + Histidine hydrochloride (0.25 + 0.006) | * |
| | Comparative examples | |
| | Sodium citrate (0.5) | ** |
| | Histidine hydrochloride (0.012) | **** |
| | Not present | **** |
| 19 | Present invention | |
| | Sodium citrate + Histidine hydrochloride (0.25 + 0.006) | * |
| | Comparative examples | |
| | Sodium citrate (0.5) | ** |
| | Histidine hydrochloride (0.012) | *** |
| | Not present | *** |
| 20 | Present invention | |
| | Sodium citrate + Sodium aspartate (0.25 + 0.06) | No change |
| | Comparative examples | |
| | Sodium citrate (0.5) | * |
| | Sodium aspartate (0.12) | *** |
| | Not present | **** |
| 21 | Present invention | |
| | Sodium citrate + Sodium aspartate (0.25 + 0.06) | No change |
| | Comparative examples | |
| | Sodium citrate (0.5) | * |
| | Sodium aspartate (0.12) | **** |
| | Not present | **** |
| 22 | Present invention | |
| | Sodium citrate + Sodium aspartate (0.25 + 0.06) | No change |
| | Comparative examples | |
| | Sodium citrate (0.5) | ** |
| | Sodium aspartate (0.12) | **** |
| | Not present | **** |
| 23 | Present invention | |
| | Sodium citrate + Sodium aspartate (0.25 + 0.06) | No change |
| | Comparative examples | |
| | Sodium citrate (0.5) | * |
| | Sodium Aspartate (0.12) | ** |
| | Not present | **** |
| 24 | Present invention | |
| | Sodium citrate + Sodium aspartate (0.25 + 0.06) | * |
| | Comparative examples | |
| | Sodium citrate (0.5) | ** |
| | Sodium aspartate (0.12) | *** |
| | Not present | **** |
| 25 | Present invention | |
| | Sodium citrate + Histidine hydrochloride (0.25 + 0.006) | No change |
| | Comparative examples | |
| | Sodium citrate (0.5) | * |
| | Histidine hydrochloride (0.012) | *** |
| | Not present | **** |
| 26 | Present invention | |
| | Sodium citrate + Sodium aspartate (0.25 + 0.06) | * |
| | Comparative examples | |
| | Sodium citrate (0.5) | ** |
| | Sodium aspartate (0.12) | **** |
| | Not present | **** |

TABLE 10-continued

| Example | Stabilizing agent[1] (part by weight) | Appearance[2] |
|---|---|---|
| 27 | Present invention | |
| | Sodium citrate + Sodium aspartate (0.25 + 0.06) | No change |
| | Comparative examples | |
| | Sodium citrate (0.5) | ** |
| | Sodium aspartate (0.12) | *** |
| | Not present | **** |
| 28 | Present invention | |
| | Sodium citrate + Histidine hydrochloride (0.25 + 0.006) | No change |
| | Comparative examples | |
| | Sodium citrate (0.5) | * |
| | Histidine hydrochloride (0.012) | ** |
| | Not present | ** |

[1] The amounts of the added stabilizing agents are shown in terms of parts by weight based on a part by weight of the lipid for forming liposomes. The amounts of the salts are represented by the amounts calculated as their free forms. (The concentration of liposome membrane forming materials was 25 mg/ml.)
[2] Appearance was examined after 2-week storage for Examples 10 to 25 and after one-week storage for Examples 26 to 28.
*: Faint yellow, : Light yellow, *: Yellow, ****: Yellowish brown Example 29

(Parenteral injection)

The aqueous dispersion containing liposomes obtained in Example 8 containing 2% of sodium citrate and 0.2% of sodium glutamate, of which liposomes encapsulated betamethasone phosphate, was diluted with phosphate buffer (pH 8.3) containing 2% of sodium citrate and 0.2% of sodium glutamate to give an aqueous dispersion containing liposomes, which contained 1 mg of betamethasone per 1 ml. The dispersion was filled into 2 ml of glass ampoules and sterilized by heating at 70° C. for 1 hour three times every 24 hours to give a parenteral injection.

Example 30

(Nasal drop)

The aqueous dispersion containing liposomes obtained in Example 8 containing 2% of sodium citrate and 0.2% of sodium glutamate, of which liposomes encapsulated betamethasone phosphate, was diluted with phosphate buffer (pH 8.3) containing 2% of sodium citrate and 0.2% of sodium glutamate and, further, added with benzalkonium chloride of which final concentration in the dispersion was 0.005% to give an aqueous dispersion containing 1 mg of betamethasone per 1 ml. This dispersion was filtered through a membrane filter of 0.22 μm and filled in a container for spraying as a nasal drop.

Example 31

(Endermic agent)

The aqueous dispersion containing liposomes obtained in Example 8 containing 2% of sodium citrate and 0.2% of sodium glutamate, of which liposomes encapsulated betamethasone phosphate, was diluted with phosphate buffer (pH 8.3) containing 2% of sodium citrate and 0.2% of sodium glutamate and, further, added with benzalkonium chloride of which final concentration in the dispersion was 0.005% to give an aqueous dispersion containing 1 mg of betamethasone per 1 ml. This dispersion was filtered through a membrane filter of 0.22 μm and filled in a plastic container with sponge as an endermic agent.

Example 32

(Inhalation agent)

The aqueous dispersion containing liposomes obtained in Example 8 containing 2% of sodium citrate and 0.2% of sodium glutamate, of which liposomes encapsulated betamethasone phosphate, was diluted with phosphate buffer (pH 8.3) containing 2% of sodium citrate and 0.2% of sodium glutamate and, further, added with benzalkonium chloride of which final concentration in the dispersion was 0.005% to give an aqueous dispersion containing 1 mg of betamethasone per 1 ml. This dispersion was filtered through a membrane filter of 0.22 μm and filled in a nebulizer container as an inhalation agent.

Example 33

(Oral agent)

The aqueous dispersion containing liposomes obtained in Example 8 containing 2% of sodium citrate and 0.2% of sodium glutamate, of which liposomes encapsulated betamethasone phosphate, was diluted with phosphate buffer (pH 8.3) containing 2% of sodium citrate and 0.2% of sodium glutamate and, further, added with D-sorbitol and potassium sorbate of which final concentrations in the dispersion were 10% and 0.1% respectively to give an aqueous dispersion containing 1 mg of betamethasone per 1 ml. This dispersion was filtered through a membrane filter of 0.45 μm and filled in a glass container as an oral agent.

Example 34

(Parenteral injection)

The aqueous dispersion containing liposomes obtained in Example 9 containing 0.2% of sodium citrate and 0.2% of sodium glutamate, of which liposomes encapsulated morphine hydrochloride, was diluted with phosphate buffer (pH 6.0) containing 0.2% of sodium citrate and 0.2% of sodium glutamate to give an aqueous dispersion containing 0.5 mg of morphine hydrochloride per 1 ml. This dispersion was filtered through a membrane filter of 0.22 μm and filled in a glass ampoule as a paranteral injection.

Example 35

(Eye drop)

The aqueous dispersion containing liposomes obtained in Example 11 containing 0.5% of sodium citrate and 0.5% of sodium glutamate, of which liposomes encapsulated timolol maleate, was diluted with phosphate buffer (pH 8.0) containing 0.5% of sodium citrate and 0.5% of sodium glutamate and, further, added with benzalkonium chloride of which final concentration in the dispersion was 0.005% to give an aqueous dispersion containing 2.5 mg of timolol per 1 ml. This dispersion was filtered through a membrane filter of 0.22 μm and filled in a 5-ml eye drop bottle as an eye drop.

Example 36

(Eye drop)

The aqueous dispersion containing obtained in Example 12 containing 0.5% of sodium citrate and 0.2% of sodium glutamate, of which liposomes encapsulated sodium dicrofenac, was diluted with phosphate buffer (pH 8.0) containing 0.5% of sodium citrate and 0.2% of sodium glutamate and, further, added with benzalkonium chloride of which final concentration in the dispersion was 0.005% to give an aqueous dispersion containing 1 mg of sodium dicrofenac per 1 ml. This dispersion was filtered through a membrane filter of 0.22 µm and filled in a 5-ml eye drop bottle as an eye drop.

According to the present invention, there are provided aqueous dispersions containing liposomes which hardly show coloration though they are composed of natural phospholipids, which are inexpensive and safe, show little leak of drugs encapsulated therein and hence are excellent in storage stability.

Moreover, since the advantages of the present invention are obtained in a broad pH range, it is possible to select a pH value suitable for stably storing the encapsulated drug and, therefore, there are provided aqueous dispersion containing liposomes wherein the storage stability of the encapsulated drug is also excellent.

What is claimed is:

1. An aqueous dispersion containing liposomes comprising one or both of yolk lecithin and soybean lecithin as lipids for forming liposomes wherein the dispersion contains citric acid or a pharmaceutically acceptable salt thereof and one or more amino acids selected from the group consisting of methionine, histidine, arginine, glutamic acid, aspartic acid and pharmaceutically acceptable salts thereof, wherein said citric acid and amino acids or pharmaceutically acceptable salts thereof, if said particular amino acid or pharmaceutically acceptable salt thereof is present, are contained in the following parts by weight ranges wherein the part by weight of the amino acid salt refers to the amount by weight expressed in terms of the particular amino acid:

citric acid or a pharmaceutically acceptable salt is present in an amount ranging from 0.05 to 5 parts by weight based on a part by weight of the lipids used to form the liposomes and not more than 0.13 parts by weight of the aqueous dispersion containing liposomes in terms of citric acid;

histidine or pharmaceutically acceptable salts thereof, if present, is or are contained in an amount expressed in terms of histidine ranging from 0.0006 to 0.3 parts by weight based on one part by weight of the lipids used to form the liposomes and not more than 0.015 parts by weight based on one part by weight of the aqueous dispersion containing liposomes;

arginine or pharmaceutically acceptable salts thereof, if present, is or are contained in an amount expressed in terms of arginine, ranging from 0.02 to 4 parts by weight based on one part by weight of the lipids used to form liposomes and not more than 0.05 parts by weight based on one part by weight of the aqueous dispersion containing liposomes;

methionine or pharmaceutically acceptable salts thereof, if present, is or are contained in an amount ranging from 0.008 to 0.8 parts by weight based on one part by weight of the lipids and to make the liposomes and not more than 0.02 parts by weight based on one part by weight of the aqueous dispersion containing liposomes; and wherein glutamic acid and aspartic acid or pharmaceutically acceptable salts thereof, if present, are contained in an amount by weight expressed in terms of glutamic acid and aspartic acid ranging from 0.015 to 3 parts by weight based on one part by weight of the lipids used to form the liposomes and not more than 0.08 parts by weight based on one part by weight of the aqueous dispersion containing liposomes; and wherein the amount of citric acid and the one or more amino acids or pharmaceutically acceptable salts thereof are sufficient to produce an aqueous dispersion containing liposomes which does not substantially change color during storage.

2. The aqueous liposome containing dispersion of claim 1 wherein color change is evaluated using a color difference meter before and after storage using coordinate values based on the UCS system of color representation, L, a and b are measured based upon the color difference of the aqueous dispersion before and after storage, and wherein relative color change, $\Delta E$, is calculated according to the equation:

$$\Delta E = \{(L_1-L_2)^2+(a_1-a_2)^2+(b_1-b_2)^2\}^{1/2}$$

and wherein an aqueous liposome composition which does not substantially change color during storage refers to a composition which possesses a $\Delta E$ of 3.5 or less.

3. The aqueous dispersion of claim 1 wherein the amount of citric acid is about 0.05 parts by weight and the amount of the amino acid or a pharmaceutically acceptable salt thereof ranges from about 0.06 to about 0.08 parts by weight.

4. The aqueous dispersion containing liposomes according to claim 1 wherein the liposomes encapsulate a drug.

5. The aqueous dispersion containing liposomes according to claim 4 wherein the drug is any one selected from the group consisting of hypnotics, sedatives, antianxiety agents, antiepileptics, antipyretics, analgesics, antiinflammatory agents, psychotropic agents, local anesthetics, antispasmodics, antihypertensives, vasoconstrictors, vasodilators, antihyperlipemnia agents, antitussives, bronchodilators, antiulcer agents, hormones, vitamins, hemostatics, enzymes, agents suitable for treatment of diabetes, carcinostatic agents, antiallergic agents, antibiotics, chemotherapeutics, antiglaucoma drugs, anticataract drugs, mydriatics, miotics, diagnostic agents, prostaglandins and immunoregulatory drugs.

6. The aqueous dispersion containing liposomes according to claim 5 wherein the drug is any one selected from the group consisting of tegafur, gentamicin, penicillamine, chlorpheniramine, cromoglicic acid, betamethasone phosphate, dexamethasone phosphate, dicrofenac, fluorometholone, pranoprofen, morphine, urokinase, lidocaine, prostaglandin $E_1$, 2-N-{3-[3-(1-piperidinomethyl)phenoxy]propyl}amino-5-amino-1,3,4-thiadiazole, timolol, glutathione, phenylephrine, tropicamide, pilocarpine, carbachol epalrestat and pharmaceutically acceptable salts thereof.

7. A pharmaceutical preparation which is in the form of a composition administrable by parenteral injection, a nasal drop, a lotion, a liniment, a composition administrable by inhalation, or a composition suitable for oral administration which comprises the aqueous dispersion containing liposomes according to claim 4.

* * * * *